(12) United States Patent
Short (10) Patent No.: US 9,468,786 B2
(45) Date of Patent: Oct. 18, 2016

(54) KITS AND METHODS FOR DISPOSING OF PHARMACEUTICALS AND SHARPS

(71) Applicant: Gregg R. Short, Solana Beach, CA (US)

(72) Inventor: Gregg R. Short, Solana Beach, CA (US)

( * ) Notice: Subject to any disclaimer, the term of this patent is extended or adjusted under 35 U.S.C. 154(b) by 0 days.

(21) Appl. No.: 14/618,209

(22) Filed: Feb. 10, 2015

(65) Prior Publication Data

US 2015/0231433 A1  Aug. 20, 2015

Related U.S. Application Data

(60) Provisional application No. 62/050,794, filed on Sep. 16, 2014, provisional application No. 61/939,934, filed on Feb. 14, 2014.

(51) Int. Cl.
| | | |
|---|---|---|
| *B09B 3/00* | (2006.01) |
| *A62D 3/30* | (2007.01) |
| *B65D 43/02* | (2006.01) |
| *A62D 3/37* | (2007.01) |
| *A61M 5/32* | (2006.01) |

(52) U.S. Cl.
CPC .............. *A62D 3/30* (2013.01); *A61M 5/3205* (2013.01); *A62D 3/37* (2013.01); *B65D 43/02* (2013.01); *A61M 2005/328* (2013.01)

(58) Field of Classification Search
CPC ..................... A61M 2005/328; B09B 3/0075; A62D 3/30
See application file for complete search history.

(56) References Cited

U.S. PATENT DOCUMENTS

| | | | | |
|---|---|---|---|---|
| 5,322,165 A * | 6/1994 | Melker | ................. | A61M 5/002 206/365 |
| 6,010,444 A * | 1/2000 | Honeycutt | ............ | B09B 3/0033 206/365 |
| 2012/0305132 A1* | 12/2012 | Maness | .............. | A61B 19/0287 141/69 |

* cited by examiner

*Primary Examiner* — John Kreck
(74) *Attorney, Agent, or Firm* — Withers & Keys, LLC (57) ABSTRACT

Methods of disposing of pharmaceuticals are disclosed. Methods of disposing of sharps are also disclosed. Pharmaceutical and sharps disposal kits are also disclosed.

20 Claims, 2 Drawing Sheets

FIG. 1

FIG. 2 after polymerization  
yellow color before polymerization  
red color

FIG. 3

KITS AND METHODS FOR DISPOSING OF PHARMACEUTICALS AND SHARPS

CROSS-REFERENCE TO RELATED APPLICATIONS

This patent application claims the benefit of priority to (i) U.S. provisional patent application Ser. No. 62/050,794 entitled "METHODS OF DISPOSING OF PHARMACEUTICALS AND SHARPS" filed on Sep. 16, 2014, and (ii) U.S. provisional patent application Ser. No. 61/939,934 entitled "METHODS OF DISPOSING OF PHARMACEUTICALS AND SHARPS" filed on Feb. 14, 2014, the subject matter of both of which is incorporated herein in its entirety.

FIELD OF THE INVENTION

The present invention relates generally to methods of disposing of pharmaceuticals and/or sharps (i.e., used syringes and needles). The present invention further relates to pharmaceutical and/or sharps disposal kits that may be used in the disclosed methods of disposing of pharmaceuticals and/or sharps.

BACKGROUND OF THE INVENTION

Methods of disposing of pharmaceuticals, such as in a home environment, typically comprise disposing of the pharmaceuticals in a waste basket with or without any packaging for the pharmaceuticals. Such conventional methods of disposing of pharmaceuticals create an unsafe, environmentally-unfriendly distribution of discarded pharmaceuticals.

Unfortunately, in a home environment, used syringes and needles are also improper disposed of in a waste basket. Although proper methods of disposing of sharps are known, many users fail to follow proper disposal methods.

There is a need in the art for simple, effective, safe and environmentally-friendly pharmaceuticals and/or sharps disposal kits, as well as methods of disposing of pharmaceuticals and/or sharps.

SUMMARY OF THE INVENTION

The present invention is directed to simple, effective, safe and environmentally-friendly methods of disposing of pharmaceuticals and/or sharps. The disclosed methods of disposing of pharmaceuticals and/or sharps efficiently and safely enable proper disposal of pharmaceuticals and/or sharps. The disclosed pharmaceutical and/or sharps disposal systems provide a cost-effective and convenient method of properly disposing of pharmaceuticals and/or sharps.

In the broadest sense, the present invention involves compositions, devices, kits and methods for collecting, dissolving, encapsulating, destroying and/or disposing of pharmaceuticals and/or sharps.

In one exemplary embodiment, the method of disposing of pharmaceuticals comprises depositing one or more pharmaceuticals into a container containing (i) a first monomeric component and (ii) water, the first monomeric component being capable of polymerization when combined with an effective amount of a polymerization initiator. The exemplary method of disposing of pharmaceuticals may further comprise one or more additional steps such as incorporating a polymerization initiator into the container in an effective amount to cause polymerization of the first monomeric component. Polymerization of the first monomeric component results in encapsulation of dissolved pharmaceuticals within a solid polymeric (e.g., acrylic) matrix that has denatured the pharmaceutical and rendered it unrecoverable and non-hazardous. Thus, the solid polymeric (e.g., acrylic) matrix can subsequently be disposed of as solid waste without the dangers associated with previously known methods of disposing of pharmaceuticals.

The present invention is also directed to pharmaceutical disposal kits. In one exemplary embodiment, the pharmaceutical disposal kit comprises (I) a container comprising a container housing surrounding a container volume, a container opening providing access to the container volume from outside the container housing, and a movable container housing closure member sized to extend over and cover the container opening; (II) a mixture of (i) a first monomeric component and (ii) water occupying at least a portion of the container volume, the first monomeric component being capable of polymerization when combined with an effective amount of a polymerization initiator; and (III) at least one pharmaceutical within the mixture. The exemplary pharmaceutical disposal kit may further comprise a polymerization initiator, in the container, in an effective amount to cause polymerization of the first monomeric component and cause complete encapsulation of dissolved pharmaceuticals into a solid acrylic matrix that has denatured the pharmaceutical and rendered it unrecoverable and non-hazardous. Thus, it can subsequently be disposed of as solid waste without the dangers associated with previously known methods of disposing of pharmaceuticals.

The present invention is further directed to methods of disposing of pharmaceuticals and/or sharps (e.g., used syringes and needles). In one exemplary embodiment, the method of disposing of pharmaceuticals and/or sharps comprises depositing one or more pharmaceuticals, one or more syringes, one or more needles, or any combination thereof into a container containing a mixture of: (i) water, (ii) a first monomeric component capable of polymerization when combined with an effective amount of a polymerization initiator, and (iii) a colorant, the colorant enabling the mixture to undergo a color change when combined with the effective amount of the polymerization initiator. Polymerization of the first monomeric component results in encapsulation of dissolved pharmaceuticals and/or sharps within a solid polymeric (e.g., acrylic) matrix that has (i) denatured the pharmaceutical and rendered it unrecoverable and non-hazardous, and/or (ii) rendered the sharps unrecognizable and unusable. Thus, the solid polymeric (e.g., acrylic) matrix can subsequently be disposed of as solid waste without the dangers associated with previously known methods of disposing of pharmaceuticals.

The present invention is even further directed to pharmaceuticals and/or sharps (e.g., used syringes and needles) disposal kits. In one exemplary embodiment, the pharmaceutical and/or sharps disposal kit comprises: (I) a container comprising: a container housing surrounding a container volume, a container opening providing access to said container volume from outside said container housing, and a movable container housing closure member sized to extend over and cover said container opening; and (II) a mixture within said container, said mixture comprising: (i) water occupying at least a portion of said container volume, (ii) a first monomeric component capable of polymerization when combined with an effective amount of a polymerization initiator, and (iii) a colorant, said colorant enabling said mixture to undergo a color change when combined with said effective amount of said polymerization initiator.

These and other features and advantages of the present invention will become apparent after a review of the following detailed description of the disclosed embodiments and the appended claims.

BRIEF DESCRIPTION OF THE FIGURES

The present invention is further described with reference to the appended figure, wherein.

DETAILED DESCRIPTION OF THE INVENTION

The present invention is directed to methods of disposing of pharmaceuticals. The present invention is further directed to pharmaceutical disposal kits.

I. Methods of Disposing of Pharmaceuticals

Figure 1:
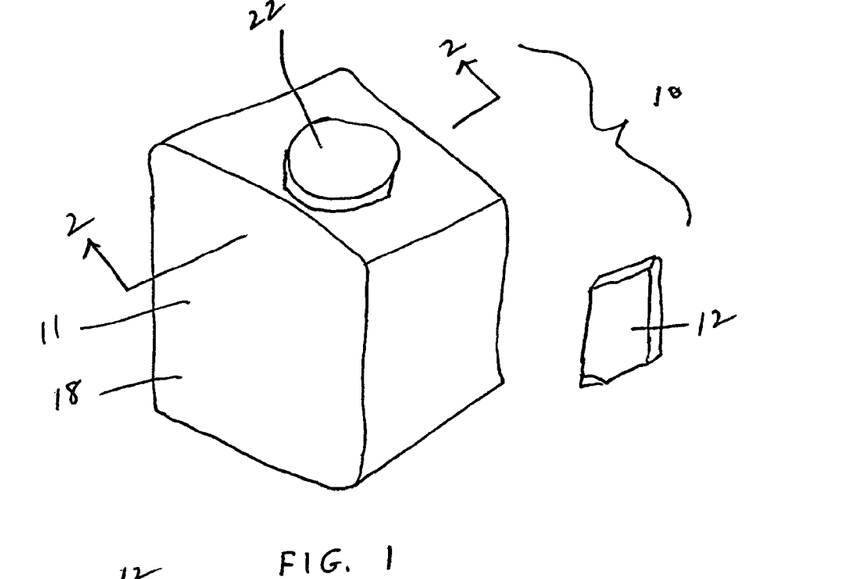
FIG. 1 depicts a perspective view of an exemplary pharmaceutical and/or sharps disposal kit of the present invention.
Figure 2:
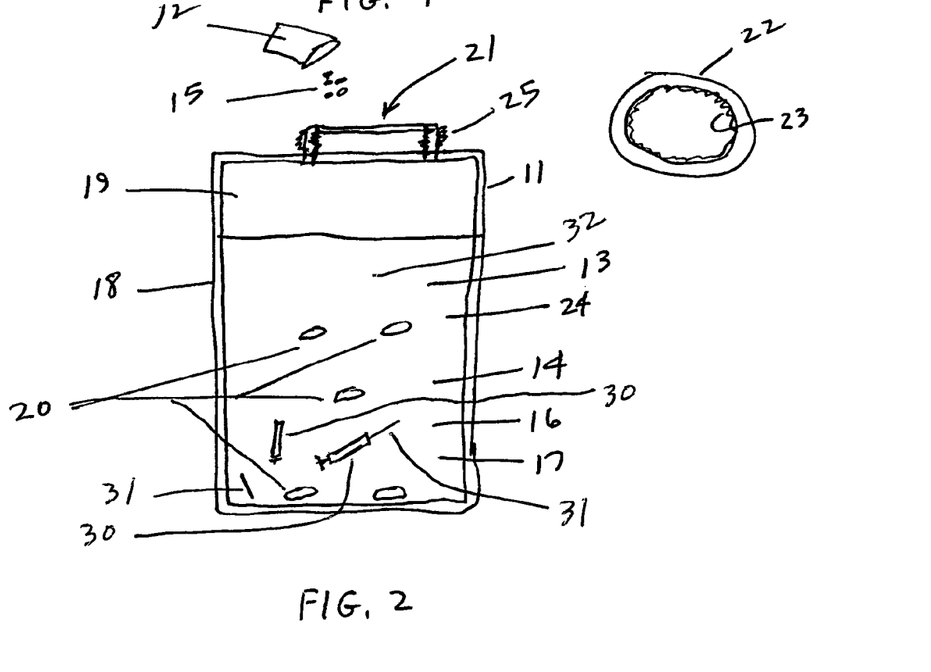
FIG. 2 depicts a cross-sectional view of the exemplary container shown in the exemplary pharmaceutical and/or sharps disposal kit of FIG. 1 as view along line 2-2 shown in FIG. 1.

The present invention is directed to methods of disposing of pharmaceuticals. FIGS. 1-2 depict an exemplary pharmaceutical disposal kit 10 that may be used in the methods of the present invention.

As discussed above, the method of disposing of pharmaceuticals may comprise disposing of one or more pharmaceuticals 20 into a container 11 containing (i) a first monomeric component 13 and (ii) water 14, wherein first monomeric component 13 is capable of polymerization when combined with an effective amount of a polymerization initiator 15. Typically, first monomeric component 13 and water 14 occupy from about 50% to about 90% of a total container volume 19 so as to provide room within container 11 for a desired amount of pharmaceuticals 20 to be placed therein. See, for example, FIG. 2.

The methods of disposing of pharmaceuticals of the present invention may further comprise one or more additional steps including, but not limited to, traveling to a "drop-off" site (e.g., a pharmacy) to deposit pharmaceuticals 20 (e.g., the user/owner of pharmaceuticals 20 can actually place the pharmaceuticals 20 in container 11 thereby eliminating any chain of custody issues or something nefarious happening to pharmaceuticals 20 before being placed in container 11; this is a huge elimination of liability and DEA concerns because disposing of whole pharmaceuticals 20 can get in the wrong hands; a disposal companies employees were recently convicted of taking pharmaceuticals 20 before incineration and selling the pharmaceuticals 20); incorporating polymerization initiator 15 into the container 11 in an effective amount to cause polymerization of the first monomeric component 13; removing movable container housing closure member 22 from container 11 to access container opening 21; attaching movable container housing closure member 22 to container 11 to close container opening 21; shaking container 11 to mix (remix) the contents within container 11; and disposing of the polymer-containing container 11 after use.

The methods of disposing of pharmaceuticals of the present invention result in a contained solid polymer matrix that encapsulates dissolved and denatured pharmaceuticals 20 placed within the container 11. The encapsulation of dissolved pharmaceuticals 20 (1) eliminates chain of custody and security concerns, (2) eliminates potential water contamination issues, (3) leverages existing waste transportation (i.e., does not create or require additional waste truck traffic like other existing disposal options), and (4) eliminates large and polluting incinerator treatment methods.

II. Pharmaceutical Disposal Kits

The present invention is further directed to pharmaceutical disposal kits such as exemplary pharmaceutical disposal kit 10 shown in FIGS. 1-2. Typically, container 11 has a container volume 19 of from about 1.0 to about 5.0 gallons, which typically provide a disposal vessel for pharmaceuticals for up to about 6 months. Container 11 may comprise a safety cap 22, which like container 11, has a small opening that does not allow a user's hand to enter container 11.

Typically, first monomeric component 13 is present in an amount ranging from about 20 weight percent (wt %) to about 90 wt % (or, in increments of 0.1 wt %, any wt % between 20 and 90 wt %, e.g., 59.7 wt %, or any range of values between 20 and 90 wt %, e.g., 60.1 to 89.3 wt %), and water 14 is present in an amount ranging from about 80 wt % to about 10 wt % (or, in increments of 0.1 wt %, any wt % between 80 and 10 wt %, e.g., 23.4 wt %, or any range of values between 80 and 10 wt %, e.g., 60.1 to 9.3 wt %), based on a total weight of the mixture 24 within container 11. When present, each of reducing agent 16 and free radical scavenger 17 is independently present in an amount ranging from about less than 1.0 wt %, more typically, about 0.01 wt % based on a total weight of the mixture 24 within container 11.

III. Methods of Disposing of Sharps (i. e., Syringes and/or Needles)

Figure 3:
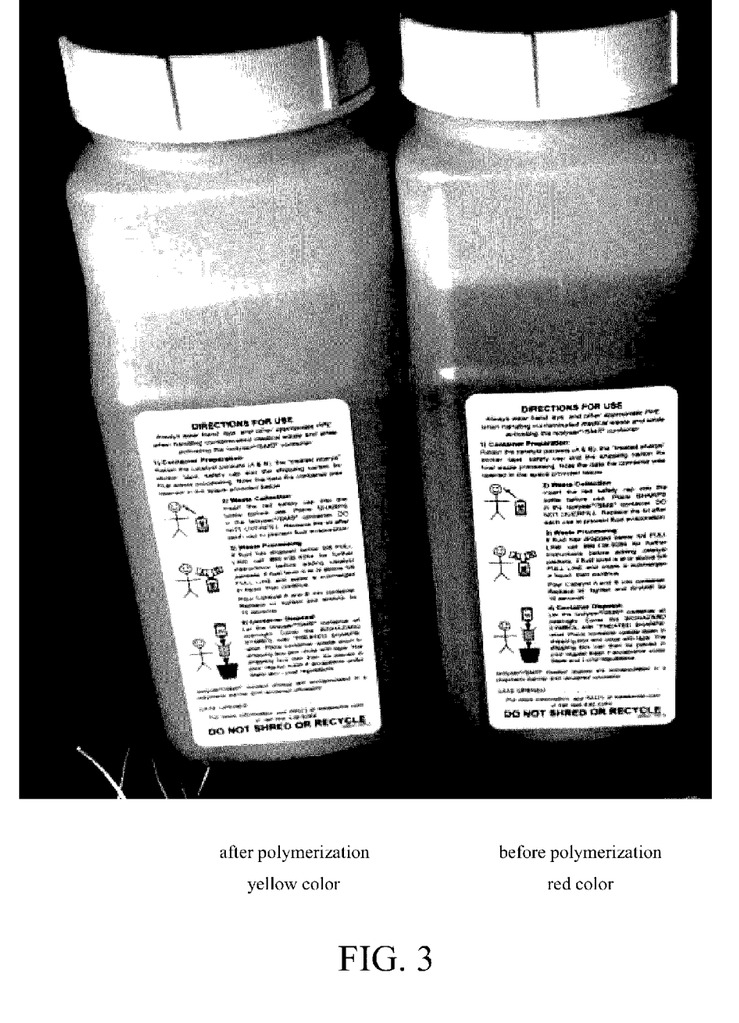
FIG. 3 depicts the color change of an exemplary mixture used in the disclosed pharmaceutical and/or sharps disposal kits of the present invention with the mixture having a red color prior to polymerization and a yellow color after polymerization.

The present invention is even further directed to methods of disposing of sharps (e.g., used syringes and needles). FIGS. 1-3 depict an exemplary sharps disposal kit 10 that may be used in the methods of the present invention.

The method of disposing of sharps may comprise disposing of one or more syringes 30, needles 31 (i.e., attached to syringe 30 or detached from syringe 30) into container 11 discussed above. In addition to (i) a first monomeric component 13 and (ii) water 14, wherein first monomeric component 13 is capable of polymerization when combined with an effective amount of a polymerization initiator 15, mixture 24 further comprises colorant 32 (e.g., a red dye). See, for example, FIG. 2.

The methods of disposing of sharps of the present invention may further comprise one or more additional steps including, but not limited to, traveling to a "drop-off" site (e.g., a pharmacy) to deposit syringes 30 and/or needles 31 (e.g., the user/owner of syringes 30 and/or needles 31 can actually place the syringes 30 and/or needles 31 in container 11 thereby eliminating any chain of custody issues or something nefarious happening to syringes 30 and/or needles 31 before being placed in container 11; this is a huge elimination of liability and concerns because of disposed syringes 30 and/or needles 31 can get in the wrong hands); incorporating polymerization initiator 15 into the container 11 in an effective amount to cause polymerization of the first monomeric component 13 and a color change of mixture 24; removing movable container housing closure member 22 from container 11 to access container opening 21; attaching movable container housing closure member 22 to container 11 to close container opening 21; shaking container 11 to mix (remix) the contents within container 11; and disposing of the polymer-containing container 11 after use.

The methods of disposing of sharps of the present invention result in a contained solid polymer matrix that encapsulates syringes 30 and/or needles 31 placed within the container 11. The encapsulation of syringes 30 and/or needles 31 (1) eliminates public health concerns, (2) eliminates potential infectious water contamination issues, (3) leverages existing waste transportation (i.e., does not create or require additional waste truck traffic like other existing disposal options), and (4) eliminates large and polluting incinerator treatment methods.

IV. Pharmaceutical and/or Sharps (i.e., Syringes and/or Needles) Disposal Kits

The present invention is even further directed to pharmaceutical, sharps, or combination pharmaceutical/sharps disposal kits such as exemplary pharmaceutical and/or sharps disposal kit 10 shown in FIGS. 1-3. Container 11 has a typical container volume 19, safety cap 22, first monomeric component 13 water 14, and when present, reducing agent 16, free radical scavenger 17 and colorant 32 as discussed above.

In one exemplary embodiment, a user would utilize any of the above-described pharmaceutical and/or sharps disposal kits and/or disposal methods in a home environment. In other exemplary embodiments, users could deposit their used/unused pharmaceuticals and/or sharps within a strategically located pharmaceutical and/or sharps disposal kit, such as at a local pharmacy. In addition, a pharmacist could utilize any of the above-described pharmaceutical and/or sharps disposal kits and/or disposal methods to dispose of both syringes (i.e., for flu shots and vaccines) and unwanted pharmaceuticals either generated by them or brought to the pharmacy by their customers.

ADDITIONAL EMBODIMENTS

Methods of Disposing of Pharmaceuticals

1. A method of disposing of pharmaceuticals 20, said method comprising: depositing of one or more pharmaceuticals 20 into a container 11 containing (i) a first monomeric component 13 and (ii) water 14, the first monomeric component 13 being capable of polymerization when combined with an effective amount of a polymerization initiator 15.
2. The method of embodiment 1, wherein the first monomeric component 13 comprises an acrylic or acrylamide monomer.
3. The method of embodiment 1 or 2, wherein the first monomeric component 13 comprises an acrylic monomer having the structure:

wherein:
R$^1$ is —COOH, —COOR$^5$, —CONHOH, —CONHCH$_2$OH, or —CONH$_2$;
R$^2$ is —H, —CH$_3$, CH$_3$CH$_2$—, or —CN;
each of R$^3$ and R$^4$ is independently —H, —CH$_3$, CH$_3$CH$_2$—, or a halogen; and
R$^5$ is a C$_{1-12}$alkyl, a C$_{1-12}$alkoxyalkyl, a C$_{1-12}$hydroxyalkyl, an acrylamide, or an alkylene-bis-acrylamide.
4. The method of any one of embodiments 1 to 3, wherein the first monomeric component 13 comprises N-methylolacrylamide, acrylic acid, acrylamide, an acrylic ester, or acrylonitrile.
5. The method of any one of embodiments 1 to 4, wherein the first monomeric component 13 comprises N-methylolacrylamide.
6. The method of any one of embodiments 1 to 5, wherein the container 11 further comprises a reducing agent 16 mixed with (i) the first monomeric component 13 and (ii) the water 14.
7. The method of embodiment 6, wherein the reducing agent 16 comprises benzotriazole, sodium nitrite, sodium-metabisulfite, isoascorbic acid, sodium sulfite, aniline, sodium sulfate, pyridine, a tertiary amine, or any combination thereof.
8. The method of embodiment 6 or 7, wherein the reducing agent 16 comprises a tertiary amine comprising tetramethylethylenediamine, N,N-dimethyl-toluedine or N,N-dihydroxyethyl-paratoluedine.
9. The method of any one of embodiments 1 to 8, wherein the container 11 further comprises a free radical scavenger 17 mixed with (i) the first monomeric component 13 and (ii) the water 14.
10. The method of embodiment 9, wherein the free radical scavenger 17 comprises hydroquinone, monoethyl ether of hydroquinone, butylated hydroxyanisole, butylated hydroxytoluene, and t-butyl hydroquinone.
11. The method of any one of embodiments 1 to 10, wherein the container 11 further comprises one or more pharmaceuticals 20 within (i) the first monomeric component 13 and (ii) the water 14.
12. The method of any one of embodiments 1 to 11, further comprising: incorporating the polymerization initiator 15 into the container 11 in an effective amount to cause polymerization of the first monomeric component 13.
13. The method of any one of embodiments 1 to 12, wherein the polymerization initiator 15 comprises zinc formaldehyde sulfoxylate, ammonium persulfate, a peroxide, or a perborate.
14. The method of any one of embodiments 1 to 13, wherein the polymerization initiator 15 comprises zinc formaldehyde sulfoxylate.
15. The method of any one of embodiments 1 to 14, wherein the container 11 comprises: a container housing 18 surrounding a container volume 19, a container opening 21 providing access to the container volume 19 from outside the container housing 18, and a movable container housing closure member 22 sized to extend over and cover the container opening 21.
35. The method of embodiments 12 to 15, wherein said incorporating step causes a mixture within the container to undergo a color change.
36. The method of any one of embodiments 1 to 15 and 35, wherein the container further comprises a colorant in addition to the first monomeric component and the water.
37. The method of any one of embodiments 1 to 15 and 35 to 36, wherein the container further comprises a colorant in addition to the first monomeric component and the water, the colorant comprising a red dye.
38. The method of embodiment 37, wherein said incorporating step causes the water within the container to undergo a color change from a red color to a yellow/orange color (or a weak yellow color or an opaque colorless solid).
39. The method of any one of embodiments 1 to 15 and 35 to 38, wherein said method further comprises: depositing one or more syringes, one or more needles, or any combination thereof into the container.

Pharmaceutical-Containing Compositions

16. A pharmaceutical-containing composition resulting from the method of any one of embodiments 1 to 15. In some embodiments, the pharmaceutical-containing composition comprises a liquid mixture comprising first monomeric component 13, water 14 and at least one pharmaceutical 20 within the liquid mixture. In other embodiments, the pharmaceutical-containing composition comprises a solid polymer matrix comprising polymerized first monomeric component 13, water 14 and at least one pharmaceutical 20 within the solid polymer matrix.

40. A composition resulting from the method of embodiment 39, said composition comprising (i) one or more pharmaceuticals 20, and at least one of (ii) one or more syringes 30 and (iii) one or more needles 31. In some embodiments, the composition comprises a liquid mixture 24 comprising first monomeric component 13, water 14, at least one pharmaceutical 20, and one or more syringes 30, one or more needles 31, or any combination within the liquid mixture 24. In other embodiments, the pharmaceutical-containing composition comprises a solid polymer matrix comprising polymerized first monomeric component 13, water 14, at least one pharmaceutical 20, and one or more syringes 30, one or more needles 31, or any combination within the solid polymer matrix.

Pharmaceutical Disposal Kits

17. A pharmaceutical disposal kit 10 comprising: (I) a container 11 comprising: a container housing 18 surrounding a container volume 19, a container opening 21 providing access to said container volume 19 from outside said container housing 18, and a movable container housing closure member 22 sized to extend over and cover said container opening 21; (II) a mixture 24 within container 11, said mixture 24 comprising: (i) water 14 occupying at least a portion of said container volume 19, (ii) a first monomeric component 13 capable of polymerization when combined with an effective amount of a polymerization initiator 15; and (III) at least one pharmaceutical 20 within said mixture 24. Pharmaceutical disposal kit 10 may further comprise an optional wall or under-the-counter mounting device for mounting container 11 along a wall surface or under a counter. As discussed above, movable container housing closure member 22 may be in the form of a safety cap to prevent a user's hand from extending into container 11.

18. The pharmaceutical disposal kit 10 of embodiment 17, wherein said first monomeric component 13 comprises an acrylic or acrylamide monomer.

19. The pharmaceutical disposal kit 10 of embodiment 17 or 18, wherein said first monomeric component 13 comprises an acrylic monomer having the structure:

wherein:
R$^1$ is —OOH, —COOR$^5$, —CONHOH, —CONHCH$_2$OH, or —CONH$_2$;
R$^2$ is —H, —CH$_3$, CH$_3$CH$_2$—, or —CN;
each of R$^3$ and R$^4$ is independently —H, —CH$_3$, CH$_3$CH$_2$—, or a halogen; and
R$^5$ is a C$_{1-12}$alkyl, a C$_{1-12}$alkoxyalkyl, a C$_{1-12}$hydroxyalkyl, an acrylamide, or an alkylene-bis-acrylamide.

20. The pharmaceutical disposal kit 10 of any one of embodiments 17 to 19, wherein said first monomeric component 13 comprises N-methylolacrylamide, acrylic acid, acrylamide, an acrylic ester, or acrylonitrile.

21. The pharmaceutical disposal kit 10 of any one of embodiments 17 to 20, wherein said first monomeric component 13 comprises N-methylolacrylamide.

22. The pharmaceutical disposal kit 10 of any one of embodiments 17 to 21, wherein said container 11 further comprises a reducing agent 16 mixed with (i) said first monomeric component 13 and (ii) said water 14.

23. The pharmaceutical disposal kit 10 of embodiment 22, wherein said reducing agent 16 comprises benzotriazole, sodium nitrite, sodium-meta-bisulfite, isoascorbic acid, sodium sulfite, aniline, sodium sulfate, pyridine, a tertiary amine, or any combination thereof.

24. The pharmaceutical disposal kit 10 of embodiment 22 or 23, wherein said reducing agent 16 comprises a tertiary amine comprising, tetramethylethylenediamine, N,N-dimethyl-toluedine or N,N-dihydroxyethyl-paratoluedine.

25. The pharmaceutical disposal kit 10 of any one of embodiments 17 to 24, wherein said container 11 further comprises a free radical scavenger 17 mixed with (i) said first monomeric component 13 and (ii) said water 14.

26. The pharmaceutical disposal kit 10 of embodiment 25, wherein said free radical scavenger 17 comprises hydroquinone, monoethyl ether of hydroquinone, butylated hydroxyanisole, butylated hydroxytoluene, and t-butyl hydroquinone.

27. The pharmaceutical disposal kit 10 of any one of embodiments 17 to 26, wherein said container 11 further comprises a polymerization initiator 15 in an effective amount to cause polymerization of said first monomeric component 13.

28. The pharmaceutical disposal kit 10 of embodiment 27, wherein said polymerization initiator 15 comprises zinc formaldehyde sulfoxylate, ammonium persulfate, a peroxide, or a perborate.

29. The pharmaceutical disposal kit 10 of embodiment 27 or 28, wherein said polymerization initiator 15 comprises zinc formaldehyde sulfoxylate.

30. The pharmaceutical disposal kit 10 of any one of embodiments 17 to 29, wherein said container volume 19 comprises up to about ten gallons (or any amount in increments of 0.1 gallons up to 10.0 gallons).

31. The pharmaceutical disposal kit 10 of any one of embodiments 17 to 30, wherein said container volume 19 comprises from about 1.0 to about 5.0 gallons (or any amount in increments of 0.1 gallons between 1.1 and 4.9 gallons).

32. The pharmaceutical disposal kit 10 of any one of embodiments 17 to 31, wherein said movable container housing closure member 22 comprises a removable lid 22 having lid engaging members 23 that engage with corresponding housing engaging members 25.

33. The pharmaceutical disposal kit 10 of any one of embodiments 27 to 32, wherein said polymerization initiator 15 is packaged separately from said first monomeric component 13 prior to being combined with said first monomeric component 13.

34. The pharmaceutical disposal kit 10 of embodiment 33, wherein said polymerization initiator 15 is packaged within a plastic bag or container 12.

41. The pharmaceutical disposal kit 10 of any one of embodiments 17 to 34, wherein said mixture 24 further comprises a colorant 32.

42. The pharmaceutical disposal kit 10 of embodiment 41, wherein said colorant 32 comprises a red dye.

43. The pharmaceutical disposal kit 10 of embodiment 41 or 42, wherein said colorant 32 undergoes a color change when said mixture 24 is contacted with said polymerization initiator 15.
44. The pharmaceutical disposal kit 10 of any one of embodiments 17 to 43, wherein said mixture 24 further comprises one or more syringes 30, one or more needles 31, or any combination thereof.

Pharmaceutical and/or Sharps Disposal Kits

45. A pharmaceutical and/or sharps disposal kit 10 comprising: (I) a container 11 comprising: a container housing 18 surrounding a container volume 19, a container opening 21 providing access to said container volume 19 from outside said container housing 18, and a movable container housing closure member 22 sized to extend over and cover said container opening 21; and (II) a mixture 24 within said container 11, said mixture 24 comprising: (i) water 14 occupying at least a portion of said container volume 19, (ii) a first monomeric component 13 capable of polymerization when combined with an effective amount of a polymerization initiator 15, and (iii) a colorant 32, said colorant 32 enabling said mixture 24 to undergo a color change when combined with said effective amount of said polymerization initiator 15.
46. The pharmaceutical and/or sharps disposal kit 10 of embodiment 45, wherein said first monomeric component 13 comprises an acrylic or acrylamide monomer.
47. The pharmaceutical and/or sharps disposal kit 10 of embodiment 45 or 46, wherein said first monomeric component 13 comprises an acrylic monomer having the structure:

wherein:
R$^1$ is —COOH, —COOR$^5$, —CONHOH, —CONHCH$_2$OH, or —CONH$_2$;
R$^2$ is —H, —CH$_3$, CH$_3$CH$_2$—, or —CN;
each of R$^3$ and R$^4$ is independently —H, —CH$_3$, CH$_3$CH$_2$—, or a halogen; and
R$^5$ is a C$_{1-12}$alkyl, a C$_{1-12}$alkoxyalkyl, a C$_{1-12}$hydroxyalkyl, an acrylamide, or an alkylene-bis-acrylamide.
48. The pharmaceutical and/or sharps disposal kit 10 of any one of embodiments 45 to 47, wherein said first monomeric component 13 comprises N-methylolacrylamide, acrylic acid, acrylamide, an acrylic ester, or acrylonitrile.
49. The pharmaceutical and/or sharps disposal kit 10 of any one of embodiments 45 to 48, wherein said first monomeric component 13 comprises N-methylolacrylamide.
50. The pharmaceutical and/or sharps disposal kit 10 of any one of embodiments 45 to 49, wherein said mixture 24 further comprises a reducing agent 16 mixed with (i) said first monomeric component 13, (ii) said water 14 and (iii) said colorant 32.
51. The pharmaceutical and/or sharps disposal kit 10 of embodiment 50, wherein said reducing agent 16 comprises benzotriazole, sodium nitrite, sodium-metabisulfite, isoascorbic acid, sodium sulfite, aniline, sodium sulfate, pyridine, a tertiary amine, or any combination thereof.
52. The pharmaceutical and/or sharps disposal kit 10 of embodiment 50 or 51, wherein said reducing agent 16 comprises a tertiary amine comprising tetramethylethylenediamine, N,N-dimethyl-toluedine or N,N-dihydroxyethyl-paratoluedine.
53. The pharmaceutical and/or sharps disposal kit 10 of any one of embodiments 45 to 52, wherein said mixture 24 further comprises a free radical scavenger 17 mixed with (i) said first monomeric component 13, (ii) said water 14 and (iii) said colorant 32.
54. The pharmaceutical and/or sharps disposal kit 10 of embodiment 53, wherein said free radical scavenger 17 comprises hydroquinone, monoethyl ether of hydroquinone, butylated hydroxyanisole, butylated hydroxytoluene, and t-butyl hydroquinone.
55. The pharmaceutical and/or sharps disposal kit 10 of any one of embodiments 45 to 54, wherein said colorant 32 comprises a red dye 32.
56. The pharmaceutical and/or sharps disposal kit 10 of embodiment 55, wherein said red dye 32 enables a color change of said mixture 24 from a red color to a yellow/orange color when combined with said effective amount of said polymerization initiator 15.
57. The pharmaceutical and/or sharps disposal kit 10 of any one of embodiments 45 to 56, wherein said container 11 further comprises a polymerization initiator 15 in an effective amount to cause polymerization of said first monomeric component 13.
58. The pharmaceutical and/or sharps disposal kit 10 of embodiment 57, wherein said polymerization initiator 15 comprises zinc formaldehyde sulfoxylate, ammonium persulfate, a peroxide, or a perborate.
59. The pharmaceutical and/or sharps disposal kit 10 of embodiment 57 or 58, wherein said polymerization initiator 15 comprises zinc formaldehyde sulfoxylate.
60. The pharmaceutical and/or sharps disposal kit 10 of any one of embodiments 45 to 59, wherein said container volume 19 comprises up to about ten gallons.
61. The pharmaceutical and/or sharps disposal kit 10 of any one of embodiments 45 to 60, wherein said container volume 19 comprises from about 1.0 to about 5.0 gallons.
62. The pharmaceutical and/or sharps disposal kit 10 of any one of embodiments 45 to 61, wherein said movable container housing closure member 22 comprises a removable lid 22 having lid engaging members 23 that engage with corresponding housing engaging members 25.
63. The pharmaceutical and/or sharps disposal kit 10 of any one of embodiments 57 to 62, wherein said polymerization initiator 15 is packaged separately from said first monomeric component 13 prior to being combined with said first monomeric component 13.
64. The pharmaceutical and/or sharps disposal kit 10 of embodiment 63, wherein said polymerization initiator 15 is packaged within a plastic bag or container 12.
65. The pharmaceutical and/or sharps disposal kit 10 of any one of embodiments 45 to 64, wherein said container 11 further comprises one or more pharmaceuticals 20, one or more syringes 30, one or more needles 31, or any combination thereof within said mixture 24.
66. The pharmaceutical and/or sharps disposal kit 10 of any one of embodiments 45 to 65, wherein said container 10 further comprises one or more syringes 30, one or more needles 31, or any combination thereof within said mixture 24.
67. The pharmaceutical and/or sharps disposal kit 10 of any one of embodiments 45 to 66, wherein said container 11 further comprises one or more pharmaceuticals 20 within said mixture 24.

Methods of Disposing of Pharmaceuticals and/or Sharps

68. A method of disposing of pharmaceutical 20 and/or sharps 30/31, said method comprising: depositing one or more pharmaceuticals 20, one or more syringes 30, one or more needles 31, or any combination thereof into a container 11 containing a mixture 24 of: (i) water 14, (ii)

a first monomeric component 13 capable of polymerization when combined with an effective amount of a polymerization initiator 15, and (iii) a colorant 32, the colorant 32 enabling the mixture 24 to undergo a color change when combined with the effective amount of the polymerization initiator 15.

69. The method of embodiment 68, wherein the first monomeric component 13 comprises an acrylic or acrylamide monomer.

70. The method of embodiment 68 or 69, wherein the first monomeric component 13 comprises an acrylic monomer having the structure:

$$(R^1)(R^2)C=C(R^3)(R^4)$$

wherein:
$R^1$ is —COOH, —COOR$^5$, —CONHOH, —CONHCH$_2$OH, or —CONH$_2$;
$R^2$ is —H, —CH$_3$, CH$_3$CH$_2$—, or —CN;
each of $R^3$ and $R^4$ is independently —H, —CH$_3$, CH$_3$CH$_2$—, or a halogen; and
$R^5$ is a C$_{1-12}$alkyl, a C$_{1-12}$alkoxyalkyl, a C$_{1-12}$hydroxyalkyl, an acrylamide, or an alkylene-bis-acrylamide.

71. The method of any one of embodiments 68 to 70, wherein the first monomeric component 13 comprises N-methylolacrylamide, acrylic acid, acrylamide, an acrylic ester, or acrylonitrile.

72. The method of any one of embodiments 68 to 71, wherein the first monomeric component 13 comprises N-methylolacrylamide.

73. The method of any one of embodiments 68 to 72, wherein the mixture 24 further comprises a reducing agent 16 mixed with (i) the first monomeric component 13, (ii) the water 14, and (iii) the colorant 32.

74. The method of embodiment 73, wherein the reducing agent 16 comprises benzotriazole, sodium nitrite, sodium-meta-bisulfite, isoascorbic acid, sodium sulfite, aniline, sodium sulfate, pyridine, a tertiary amine, or any combination thereof.

75. The method of embodiment 73 or 74, wherein the reducing agent 16 comprises a tertiary amine comprising tetramethylethylenediamine, N,N-dimethyl-toluedine or N,N-dihydroxyethyl-paratoluedine.

76. The method of any one of embodiments 68 to 75, wherein the mixture 24 further comprises a free radical scavenger 17 mixed with (i) the first monomeric component 13, (ii) the water 14, and (iii) the colorant 32.

77. The method of embodiment 76, wherein the free radical scavenger 17 comprises hydroquinone, monoethyl ether of hydroquinone, butylated hydroxyanisole, butylated hydroxytoluene, and t-butyl hydroquinone.

78. The method of any one of embodiments 68 to 77, wherein the mixture 24 further comprises one or more pharmaceuticals 20, one or more syringes 30, one or more needles 31, or any combination thereof.

79. The method of any one of embodiments 68 to 78, wherein the mixture 24 further comprises one or more syringes 30, one or more needles 31, or any combination thereof.

80. The method of any one of embodiments 68 to 79, wherein the mixture 24 further comprises one or more pharmaceuticals 20.

81. The method of any one of embodiments 68 to 80, wherein the colorant 32 comprises a red dye.

82. The method of any one of embodiments 68 to 81, further comprising: incorporating the polymerization initiator 15 into the container 11 in an effective amount to cause polymerization of the first monomeric component 13.

83. The method of any one of embodiments 68 to 82, wherein the polymerization initiator 15 comprises zinc formaldehyde sulfoxylate, ammonium persulfate, a peroxide, or a perborate.

84. The method of any one of embodiments 68 to 83, wherein the polymerization initiator 15 comprises zinc formaldehyde sulfoxylate.

85. The method of any one of embodiments 68 to 84, wherein the container 11 comprises: a container housing 18 surrounding a container volume 19, a container opening 21 providing access to the container volume 19 from outside the container housing 18, and a movable container housing closure member 22 sized to extend over and cover the container opening 21.

Pharmaceutical- and/or Sharps-Containing Compositions

86. A composition resulting from the method of any one of embodiments 68 to 85. In some embodiments, the composition comprises a liquid mixture 24 comprising first monomeric component 13, water 14, colorant 32, and one or more of (i) one or more pharmaceuticals 20, (ii) one or more syringes 30, and (iii) one or more needles 31 within the liquid mixture 24. In other embodiments, the composition comprises a solid polymer matrix comprising polymerized first monomeric component 13, water 14, colorant 32, and one or more of (i) one or more pharmaceuticals 20, (ii) one or more syringes 30, and (iii) one or more needles 31 within the solid polymer matrix.

In addition, it should be understood that although the above-described pharmaceutical and/or sharps disposal kits and methods are described as "comprising" one or more components or steps, the above-described pharmaceutical and/or sharps disposal kits and methods may "comprise," "consists of," or "consist essentially of" the above-described components or steps of the pharmaceutical and/or sharps disposal kits and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a pharmaceutical and/or sharps disposal kit and/or method that "comprises" a list of elements (e.g., components or steps) is not necessarily limited to only those elements (or components or steps), but may include other elements (or components or steps) not expressly listed or inherent to the pharmaceutical and/or sharps disposal kit and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a pharmaceutical and/or sharps disposal kit and and/or a method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described pharmaceutical and/or sharps disposal kits and/or methods may comprise, consist essentially of, or consist of any of the herein-described components and features, as shown in the figures with or without any feature(s) not shown in the figures. In other words, in some embodiments, the pharmaceutical and/or sharps disposal kits of the present invention do not have any additional features other than those shown in the figures, and such additional features, not shown in the figures, are specifically excluded from the pharmaceutical and/or sharps disposal kits. In other embodiments, the pharmaceutical and/or sharps disposal kits of the present invention do have one or more additional features that are not shown in the figures.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Pharmaceutical and/or sharps disposal kits similar to exemplary pharmaceutical and/or sharps disposal kit 10 shown in FIGS. 1-3 were prepared and utilized in a home environment, as well as a commercial environment (e.g., a pharmacy). Each mixture within a given pharmaceutical and/or sharps disposal kit had one of the following compositions:

Formulation 1:
Water—73.8 wt %
N-methylolacrylamide—26 wt %
Sodium Nitrite—0.1 wt %
Benzotriazole—0.1 wt %
Formulation 2:
Water—73.75 wt %
N-methylolacrylamide—26 wt %
Sodium Nitrite—0.1 wt %
Benzotriazole—0.1 wt %
Red Dye—0.05 wt %

Each kit also contained a separate package of polymerization initiator comprising either ammonium persulfate or zinc formaldehyde sulfoxylate.

Upon polymerization of the mixtures of Formulation 2, the mixture turns from a red color to a yellow color (i.e., a very pale yellow; could also be described as a colorless opaque solid) as shown in FIG. 3.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A pharmaceutical and/or sharps disposal kit comprising:
   a container comprising:
      a container housing surrounding a container volume,
      a container opening providing access to said container volume from outside said container housing, and
      a movable container housing closure member sized to extend over and cover said container opening;
   a mixture within said container, said mixture comprising:
      water occupying at least a portion of said container volume,
      a first monomeric component capable of polymerization when combined with an effective amount of a polymerization initiator, and
      a red colorant, said red colorant enabling said mixture to undergo a color change when combined with said effective amount of said polymerization initiator; and
   an effective amount of a polymerization initiator so as to cause polymerization of the first monomeric component, the polymerization initiator comprising zinc formaldehyde sulfoxylate, ammonium persulfate, a peroxide, or a perborate;
   wherein addition of the effective amount of the polymerization initiator into the mixture causes the mixture within the container to undergo (a) polymerization and (b) a color change from (i) a red color to (ii) a yellow color or a colorless opaque condition.

2. The pharmaceutical and/or sharps disposal kit of claim 1, wherein said container volume comprises from about 1.0 to about 5.0 gallons.

3. The pharmaceutical and/or sharps disposal kit of claim 1, wherein said container further comprises one or more pharmaceuticals, one or more syringes, one or more needles, or any combination thereof within said mixture.

4. The pharmaceutical and/or sharps disposal kit of claim 3, wherein said container further comprises one or more syringes, one or more needles, or any combination thereof within said mixture.

5. The pharmaceutical and/or sharps disposal kit of claim 1, wherein the first monomeric component comprises an acrylic monomer having the structure:

$$(R^1)(R^2)C=C(R^3)(R^4)$$

wherein:
   $R^1$ is —COOH, —COOR$^5$, —CONHOH, —CONHCH$_2$OH, or —CONH$_2$;
   $R^2$ is —H, —CH$_3$, CH$_3$CH$_2$—, or —CN;
   each of $R^3$ and $R^4$ is independently —H, —CH$_3$, CH$_3$CH$_2$—, or a halogen; and
   $R^5$ is a $C_{1-12}$alkyl, a $C_{1-12}$alkoxyalkyl, a $C_{1-12}$hydroxyalkyl, an acrylamide, or an alkylene-bis-acrylamide.

6. The pharmaceutical and/or sharps disposal kit of claim 5, wherein the first monomeric component comprises N-methylolacrylamide.

7. The pharmaceutical and/or sharps disposal kit of claim 5, wherein the mixture further comprises:
   a reducing agent mixed with (i) the first monomeric component and (ii) the water, the reducing agent comprising a combination of benzotriazole and sodium nitrite; and
   a free radical scavenger mixed with (i) the first monomeric component and (ii) the water.

8. The pharmaceutical and/or sharps disposal kit of claim 1, wherein said polymerization initiator is packaged separately from said first monomeric component prior to being combined with said first monomeric component.

9. A method of using the pharmaceutical and/or sharps disposal kit of claim 1, said method comprising:
depositing one or more syringes, one or more needles, or any combination thereof into the mixture within the container; and
incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

10. A method of using the pharmaceutical and/or sharps disposal kit of claim 5, said method comprising:
depositing one or more syringes, one or more needles, or any combination thereof into the mixture within the container; and
incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

11. A method of using the pharmaceutical and/or sharps disposal kit of claim 7, said method comprising:
depositing one or more syringes, one or more needles, or any combination thereof into the mixture within the container; and
incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

12. A pharmaceutical and/or sharps disposal kit comprising:
a container comprising:
a container housing surrounding a container volume,
a container opening providing access to said container volume from outside said container housing, and
a movable container housing closure member sized to extend over and cover said container opening;
a mixture within said container, said mixture comprising:
water occupying at least a portion of said container volume,
a first monomeric component capable of polymerization when combined with an effective amount of a polymerization initiator, said first monomeric component comprising an acrylic monomer having the structure:

$$(R^1)(R^2)C=C(R^3)(R^4)$$

wherein:
$R^1$ is —COOH, —COOR$^5$, —CONHOH, —CONHCH$_2$OH, or —CONH$_2$,
$R^2$ is —H, —CH$_3$, CH$_3$CH$_2$—, or —CN,
each of $R^3$ and $R^4$ is independently —H, —CH$_3$, CH$_3$CH$_2$—, or a halogen, and
$R^5$ is a C$_{1-12}$alkyl, a C$_{1-12}$alkoxyalkyl, a C$_{1-12}$hydroxyalkyl, an acrylamide, or an alkylene-bis-acrylamide,
a red colorant, said red colorant enabling said mixture to undergo a color change when combined with said effective amount of said polymerization initiator,
a reducing agent comprising a combination of benzotriazole and sodium nitrite, and
a free radical scavenger; and
an effective amount of a polymerization initiator so as to cause polymerization of the first monomeric component, the polymerization initiator comprising zinc formaldehyde sulfoxylate, ammonium persulfate, a peroxide, or a perborate;
wherein addition of the polymerization initiator into the mixture causes the mixture within the container to undergo a color change from (i) a red color to (ii) a yellow color or a colorless opaque condition.

13. The pharmaceutical and/or sharps disposal kit of claim 12, wherein said polymerization initiator is packaged separately from said first monomeric component prior to being combined with said first monomeric component.

14. The pharmaceutical and/or sharps disposal kit of claim 13, in combination with one or more syringes, one or more needles, or any combination thereof.

15. The pharmaceutical and/or sharps disposal kit of claim 13, further comprising one or more syringes, one or more needles, or any combination thereof within said mixture.

16. The pharmaceutical and/or sharps disposal kit of claim 15, wherein said effective amount of the polymerization initiator is within said mixture, and said mixture (a) has polymerized and (b) has undergone a color change from (i) an initial red color to (ii) a yellow color or a colorless opaque condition.

17. A method of using the pharmaceutical and/or sharps disposal kit of claim 12, said method comprising:
depositing one or more syringes, one or more needles, or any combination thereof into the mixture within the container; and
incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

18. A method of using the pharmaceutical and/or sharps disposal kit of claim 13, said method comprising:
depositing one or more syringes, one or more needles, or any combination thereof into the mixture within the container; and
incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

19. A pharmaceutical and/or sharps disposal kit comprising:
a container comprising:
a container housing surrounding a container volume,
a container opening providing access to said container volume from outside said container housing, and
a movable container housing closure member sized to extend over and cover said container opening;
a mixture within said container, said mixture comprising:
water occupying at least a portion of said container volume,
a first monomeric component capable of polymerization when combined with an effective amount of a polymerization initiator, said first monomeric component comprising an acrylic monomer having the structure:

$$(R^1)(R^2)C=C(R^3)(R^4)$$

wherein:
R$^1$ is —COOH, —COOR$^5$, —CONHOH, —CONHCH$_2$OH, or —CONH$_2$,
R$^2$ is —H, —CH$_3$, CH$_3$CH$_2$—, or —CN,
each of R$^3$ and R$^4$ is independently —H, —CH$_3$, CH$_3$CH$_2$—, or a halogen, and
R$^5$ is a C$_{1-12}$alkyl, a C$_{1-12}$alkoxyalkyl, a C$_{1-12}$hydroxyalkyl, an acrylamide, or an alkylene-bis-acrylamide,
a red colorant, said red colorant enabling said mixture to undergo a color change when combined with said effective amount of said polymerization initiator,
a reducing agent comprising a combination of benzotriazole and sodium nitrite,
a free radical scavenger, and
one or more syringes, one or more needles, or any combination thereof within the mixture within the container; and an effective amount of a polymerization initiator so as to cause polymerization of the first monomeric component, the polymerization initiator (a) comprising zinc formaldehyde sulfoxylate, ammonium persulfate, a peroxide, or a perborate, and (b) being packaged separately from said first monomeric component;

wherein addition of the polymerization initiator into the mixture causes the mixture within the container to undergo a color change from (i) a red color to (ii) a yellow color or a colorless opaque condition.

20. A method of using the pharmaceutical and/or sharps disposal kit of claim 19, said method comprising:

incorporating the polymerization initiator into the container in an effective amount to cause polymerization of the first monomeric component, wherein said incorporating step causes the mixture within the container to undergo a color change from (i) a red color to (ii) a yellow color or a colorless opaque condition.

* * * * *